(12) United States Patent
Rohr et al.

(10) Patent No.: US 9,337,831 B2
(45) Date of Patent: *May 10, 2016

(54) CAPACITIVE WIRE SENSING FOR FURNITURE

(75) Inventors: William Robert Rohr, Joplin, MO (US); Ryan Edward Chacon, Carthage, MO (US)

(73) Assignee: L&P Property Management Company, South Gate, CA (US)

( * ) Notice: Subject to any disclaimer, the term of this patent is extended or adjusted under 35 U.S.C. 154(b) by 594 days.

This patent is subject to a terminal disclaimer.

(21) Appl. No.: 13/346,386

(22) Filed: Jan. 9, 2012

(65) Prior Publication Data

US 2013/0176040 A1 Jul. 11, 2013

(51) Int. Cl.
| | |
|---|---|
| *G01R 27/26* | (2006.01) |
| *H03K 17/955* | (2006.01) |
| *G01N 27/22* | (2006.01) |
| *A61B 5/11* | (2006.01) |
| *A61B 5/00* | (2006.01) |

(52) U.S. Cl.
CPC ............ *H03K 17/955* (2013.01); *G01N 27/221* (2013.01); *G01R 27/2605* (2013.01); *A61B 5/11* (2013.01); *A61B 5/6891* (2013.01); *H03K 2217/96078* (2013.01)

(58) Field of Classification Search
CPC ............ G01N 27/221; G01R 27/2605; A61B 5/1115; A61B 5/11; A61B 2562/0214
USPC .......................................... 324/663, 686, 658
See application file for complete search history.

(56) References Cited

U.S. PATENT DOCUMENTS

| | | | |
|---|---|---|---|
| 3,372,319 | A | 3/1968 | Rhodes |
| 3,971,371 | A | 7/1976 | Bloom |
| 3,991,746 | A | 11/1976 | Hanna et al. |
| 5,235,319 | A | 8/1993 | Hill |
| 5,260,666 | A | 11/1993 | Dishman et al. |
| 6,025,782 | A | 2/2000 | Newham |

(Continued)

FOREIGN PATENT DOCUMENTS

WO 0211585 A1 2/2002

OTHER PUBLICATIONS

International Search Report with Written Opinion dated May 16, 2014 in Application No. PCT/US2014/12797, 13 pages.

(Continued)

*Primary Examiner* — Amy He
(74) *Attorney, Agent, or Firm* — Shook Hardy & Bacon, L.L.P.

(57) ABSTRACT

A system and method for incorporating presence-sensing technology into furniture is provided. More particularly, the invention relates to incorporating a conductive medium into the periphery of a furniture item, such as an adjustable bed, for detecting the presence of a user or other body. The bed includes a mattress with a covering material and a tape edge surrounding the perimeter of the mattress. A capacitive wire is coupled the tape edge, and is adapted to have a voltage based on proximity of an object to the capacitive wire. The bed also includes a processor coupled to the capacitive wire. The processor receives information provided by the capacitive wire, determines when a change in voltage satisfies a threshold, and indicates whether presence is detected. Based on a determination of presence, or lack of presence, a variety of corresponding features of the adjustable bed may be activated.

16 Claims, 5 Drawing Sheets

(56) References Cited

U.S. PATENT DOCUMENTS

| | | | |
|---|---|---|---|
| 6,067,019 A * | 5/2000 | Scott ........................... | 340/573.4 |
| 6,283,504 B1 | 9/2001 | Stanley et al. | |
| 6,768,420 B2 | 7/2004 | McCarthy et al. | |
| 6,946,853 B2 | 9/2005 | Gifford et al. | |
| 7,135,983 B2 | 11/2006 | Filippov et al. | |
| 7,190,277 B2 | 3/2007 | Fultz et al. | |
| 8,397,324 B2 | 3/2013 | Hayes et al. | |
| 8,427,450 B2 | 4/2013 | Lin | |
| 2003/0011225 A1 * | 1/2003 | Barcesat .................... | 297/217.3 |
| 2005/0088264 A1 | 4/2005 | Iwasaki | |
| 2006/0164254 A1 | 7/2006 | Kamizono et al. | |
| 2006/0261769 A1 | 11/2006 | Rees | |
| 2009/0119841 A1 | 5/2009 | Takashima | |
| 2009/0211818 A1 | 8/2009 | Kondo | |
| 2010/0096899 A1 * | 4/2010 | Kato et al. ............... | 297/452.58 |
| 2011/0209287 A1 | 9/2011 | Call et al. | |
| 2011/0221459 A1 | 9/2011 | Uno et al. | |
| 2012/0025991 A1 | 2/2012 | O'Keefe et al. | |
| 2013/0174343 A1 * | 7/2013 | Chacon et al. .................... | 5/613 |
| 2013/0176040 A1 | 7/2013 | Rohr et al. | |
| 2013/0247302 A1 * | 9/2013 | Chacon et al. .................... | 5/613 |

OTHER PUBLICATIONS

Non-Final Office Action dated Jun. 19, 2014 in U.S. Appl. No. 13/346,386, 17 pages.
Non-Final Office Action dated Jul. 7, 2014 in U.S. Appl. No. 13/749,120, 21 pages.
International Search Report with Written Opinion dated Aug. 29, 2014 in Application No. PCTUS1432555, 8 pages.
Non-Final Office Action dated Nov. 20, 2014 in U.S. Appl. No. 13/854,720, 12 pages.
Final Office Action dated Dec. 18, 2014 in U.S. Appl. No. 13/749,120, 19 pages.
Notice of Allowance dated Mar. 20, 2015 in U.S. Appl. No. 13/854,720, 8 pages.
Non-Final Office Action dated Apr. 28, 2015 in U.S. Appl. No. 13/749,120, 15 pages.
International Preliminary Report on Patentability dated Aug. 6, 2015 in Application No. PCT/US2014/012797, 7 pages.
Final Office Action dated Oct. 28, 2015 in U.S. Appl. No. 13/749,120, 16 pages.
International Preliminary Report on Patentability dated Oct. 15, 2015 in Application No. PCT/US14/32555, 7 pages.

* cited by examiner

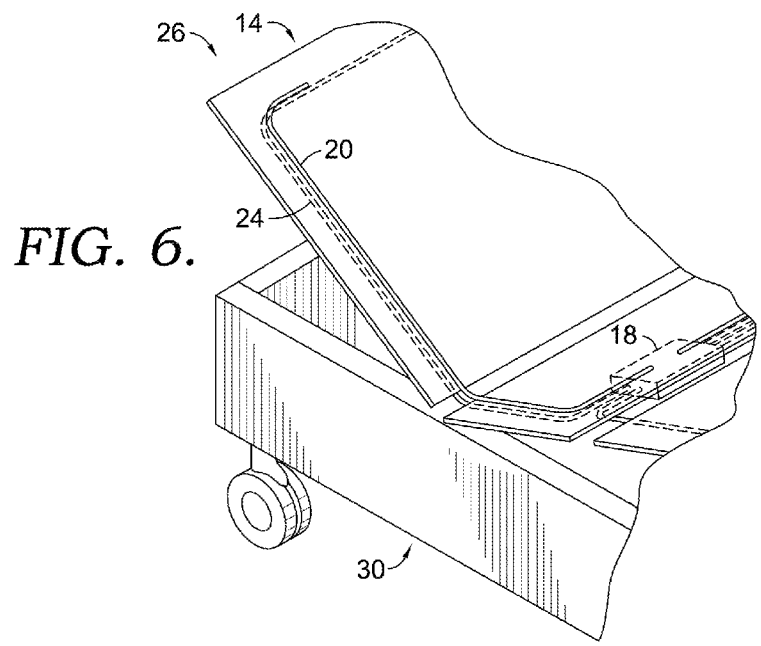
FIG. 6.
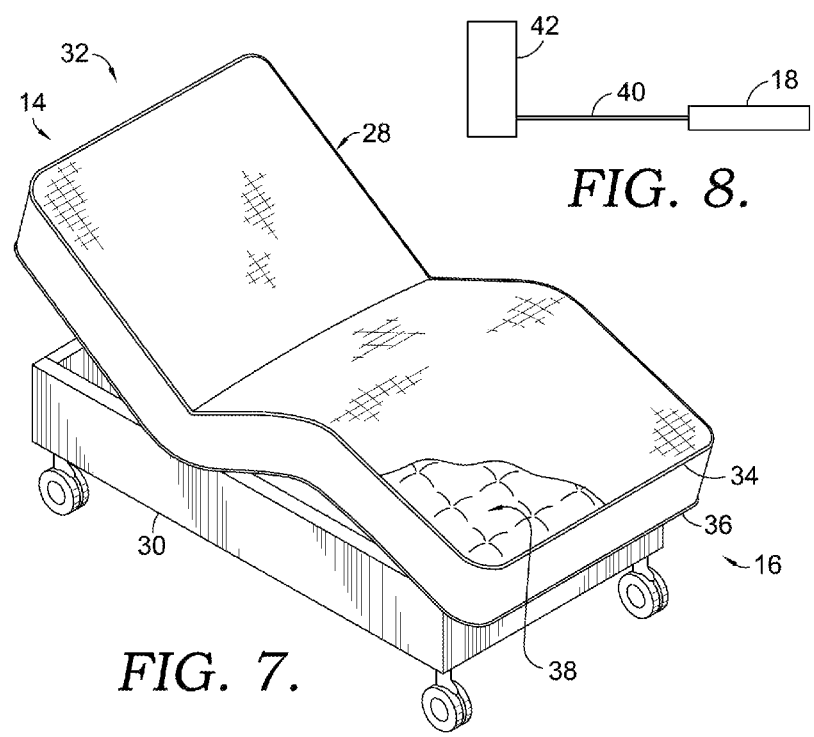
FIG. 7.
FIG. 8.

CAPACITIVE WIRE SENSING FOR FURNITURE

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention generally relates to presence-sensing technology incorporated into furniture. More particularly, the invention relates to incorporating a conductive medium into the periphery of a furniture item, such as a bed, for detecting the presence of a user or other body.

BACKGROUND OF THE INVENTION

A variety of features may be integrated into automated furniture items, including those designed to raise, lower, and generally conform to the comfort specifications of a user. Such automation may also include enhanced features that detect the presence of a person or other body, and elicit the corresponding automated response, such as stopping bed articulation or operating lighting in response to presence detection. For example, presence-sensing technology may be used to stop bed articulation to prevent an unintentional "pinch point," if the automated bedding system would otherwise be unaware of a person's presence.

Traditional presence-sensing technology for automated bedding systems utilize sensing or switches routed around the perimeter of a mattress. However, such switches can be expensive or impractical from a manufacturing standpoint. For example, presence-sensing switches may shift or bend during bed articulation, causing inaccurate readings and misplacement of the sensors. In applying upholstery to furniture items, a switch may already be compressed if the upholstery is pulled too tight. Pressure pads and switches may also be problematic in presence detection when a switch fails to be triggered by a person's presence. Alternatively, the same switches may be too sensitive, and activate independently from a body's presence. Additional analog components are required for presence detection in traditional technologies, using sensors/oscillators in addition to a circuit that detects a change.

Accordingly, a need exists for a reliable presence-sensing technology for use with furniture, such as an automated bedding system, which addresses the foregoing and other problems.

BRIEF SUMMARY OF THE INVENTION

The present invention generally relates to an apparatus for presence detection that incorporates a capacitive component into furniture items, including automated bedding systems. It should be understood that the invention contemplates incorporating a capacitive component, such as a capacitive wire, into a variety of furniture items, both bedding and otherwise, and that the invention is not limited to the specific item for which presence detection is provided. Additionally, the present invention is described as detecting/sensing presence of a person or other being using exemplary components such as a capacitive component, capacitive wire, segments of a capacitive wire, and a processor. Although a final determination of presence may be conducted using a processor and/or software associated with the claimed apparatus, reference to sensing and/or detection "by" the capacitive component, or a determination thereof by the processor, is not meant to be limiting. For example, a conductive signal detected by capacitive wires may be processed by software associated with a processor in a control enclosure, and such processing may result in a final determination of presence. In other words, a conductive wire could be described as having "detected" presence, even though the detection determination was ultimately made in software associated with a processor.

In one embodiment, a capacitive component is secured around the perimeter of a platform of an adjustable bed. For example, a capacitive wire may be secured to a perimeter of a top and bottom surface of a platform of an adjustable bed. In another embodiment, a capacitive wire is incorporated inside the tape edge applied to the perimeter of a mattress cover. In a further embodiment, capacitive wiring is integrated into the frame supporting an automated bedding system. A capacitive wire thread may also be woven into a pattern in a quilted mattress covering, in some embodiments. Exemplary embodiments of the invention include a control enclosure coupled to the capacitive component (or capacitive wire/thread) that is associated with a processor that receives presence-detecting data via the capacitive component. Software associated with the control enclosure and the capacitive wires may then make a determination of presence of a body with respect to a bedding system. Based on a determination of presence, or lack thereof, a corresponding feature of the automated bedding system may be activated.

One illustrative embodiment of an adjustable bed comprises a mattress support that comprises a plurality of support panels. At least one of the support panels is movable relative to the other ones of said support panels to thereby adjust the bed. The adjustable bed further comprises a mattress resting on top of the mattress support, where the mattress has a covering material disposed over at least a top surface of the mattress, and at least one capacitive component coupled to the bed. The capacitive component is adapted to have a voltage based on the proximity of an object to the capacitive component. The adjustable bed further comprises a processor coupled to the capacitive component, and the processor is adapted to receive information provided by the capacitive component and to determine that a change in voltage satisfies a threshold.

In another illustrative aspect, the present invention includes a method for detecting presence with respect to a bed. The method includes receiving information provided by at least one capacitive component coupled to a perimeter of the bed, wherein the capacitive component is adapted to have a voltage based on the proximity of an object to the capacitive component; determining that a change in voltage satisfies a threshold amount; and based on determining that the threshold amount is satisfied, initiating a corresponding response.

According to a third illustrative aspect, the present invention includes a bed comprising a mattress having a covering material disposed over at least a top surface of the mattress, and a tape edge surrounding a perimeter of the top surface of the mattress, the tape edge coupled to the covering material. The bed further comprises at least one capacitive component coupled to at least a portion of the tape edge, wherein the capacitive component is adapted to have a voltage based on the proximity of an object to the capacitive component. The bed still further comprises a processor coupled to the capacitive component, the processor being adapted to receive information provided by the capacitive component and to determine that a change in voltage satisfies a threshold.

Additional objects, advantages, and novel features of the invention will be set forth in part in the description which follows, and in part will become apparent to those skilled in the art upon examination of the following, or may be learned by practice of the invention.

BRIEF DESCRIPTION OF SEVERAL VIEWS OF THE DRAWING

The present invention is described in detail below with reference to the attached drawing figures, wherein:

FIG. 6 is an enlarged, perspective view of the automated bed of FIG. 5, with a capacitive wire coupled to the top of the platform and hidden lines indicating the capacitive wire and control enclosure coupled to the bottom of the platform;

FIG. 7 is a perspective view of an automated bed with a capacitive wire incorporated into the tape edge of the mattress cover;

FIG. 8 is a side view of a capacitive wire coupled to a control enclosure and an inner spring of a mattress;

DETAILED DESCRIPTION OF THE INVENTION

Figure 1:
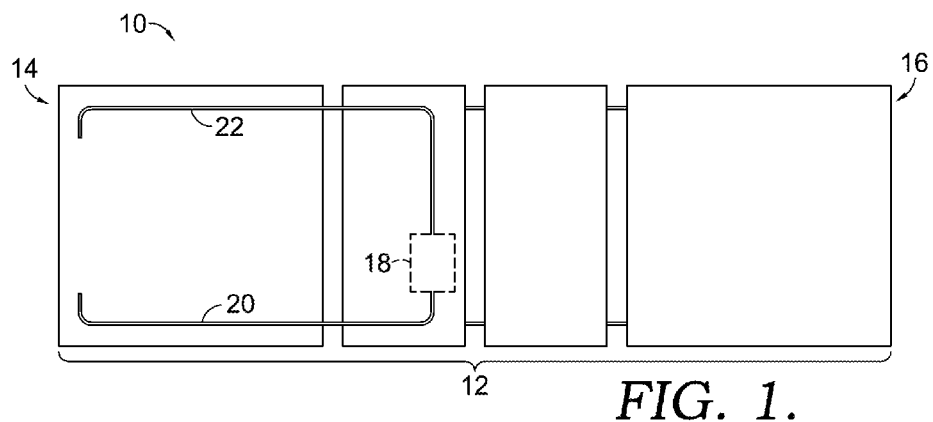
FIG. 1 is a top view of a capacitive wire coupled to the panels of an automated bed platform.

An embodiment of an automated bedding system 10 with capacitive wire sensing is seen in FIGS. 1-6. Referring first to FIG. 1, a top view of the platform of the automated bedding system 10 includes a plurality of panels 12 having a first end 14 and a second end 16, a control enclosure 18 (mounted below the panels 12), a first segment 20 of a capacitive wire, and a second segment 22 of a capacitive wire. In some embodiments, the first end 14 may be referred to as the "head" of the bed, while the second end 16 may be referred to as the "foot" of the bed.

When viewed from the top in FIG. 1, capacitive wiring is generally arranged near the first end 14 of the automated bedding system 10. A capacitive component, such as a capacitive wire, is adapted to have a voltage based on proximity of an object to the capacitive component. In some embodiments, the capacitive wire segments are standard conductive copper wires. The capacitance measured across such wires may be monitored by a processor that uses software to generate a determination of presence detection. In one embodiment, the Microchip® brand capacitive sensor may be used to determine when presence is detected. As such, while presence detection relies on the juxtaposition of a person or body with respect to the capacitive wiring, a determination of the level of detection or the measurement of presence is conducted digitally, in software associated with the processor.

As shown in FIG. 1, the capacitive wiring first and second segments 20 and 22 are coupled to the control enclosure 18, which is mounted below the panels 12 of the bedding system 10. In some embodiments, first and second segments 20 and 22 are made from a single capacitive wire, while in other embodiments, two separate capacitive wire segments 20 and 22 are coupled to the control enclosure 18. As will be understood, additional capacitive components, such as capacitive wire segments, may be coupled to the control enclosure 18, and arranged on the top of the plurality of panels 12. For example, additional capacitive wires arranged perpendicular to each other may be coupled to the control enclosure 18. In further embodiments, first and second segments 20 and 22 are made from a capacitive material other than wire.

Capacitive wire segments 20 and 22 may be used to detect presence or absence of a person or other being on top of the automated bedding system 10. For example, as arranged near first end 14 of the automated bedding system 10, the torso of a person positioned on the top of the automated bedding system 10 may be detected by capacitive wire segments 20 and 22. In embodiments, capacitive wire segments 20 and 22 create a defined sensing area on the top half of the head of the bedding system 10, and are less susceptible to noise interference from articulation of the rest of the automated bedding system 10.

Figure 2:
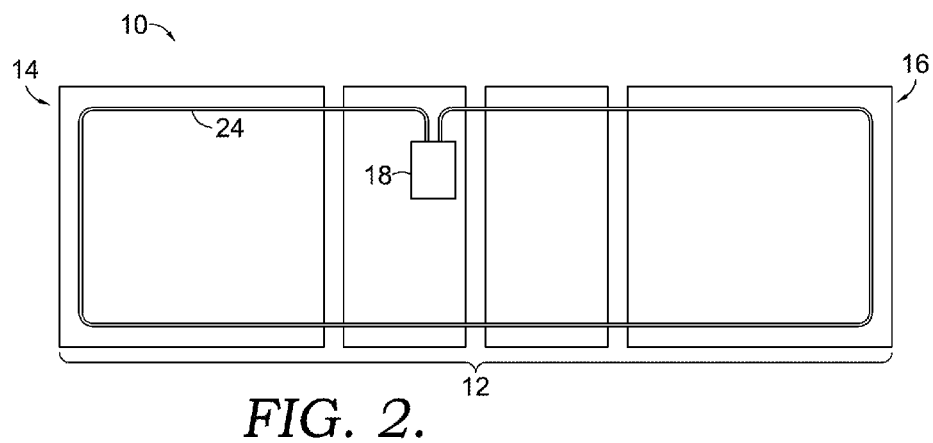
FIG. 2 is a bottom view of the automated bed platform of FIG. 1, with a capacitive wire and a control enclosure coupled to the panels.

Referring next to FIG. 2, a bottom view of the platform of the automated bedding system 10 includes the plurality of panels 12 having a first end 14 and a second end 16, a control enclosure 18, and a third segment 24 of capacitive wire. As shown in FIG. 2, the capacitive wiring third segment 24 is coupled to the control enclosure 18, which is mounted below the panels 12. In further embodiments, the control enclosure may be mounted in a different location on the bedding system 10, or may be external to the bedding system 10.

In some embodiments, third segment 24 is made from a single capacitive wire, while in other embodiments, multiple capacitive wire segments are coupled to the control enclosure 18. As will be understood, additional capacitive components, such as capacitive wire segments, may be coupled to the control enclosure 18, and arranged on the bottom of the plurality of panels 12. For example, additional capacitive wires arranged perpendicular to each other may be coupled to the control enclosure 18. In further embodiments, third segment 24 is made from a capacitive material other than wire.

Capacitive wire segment 24 may be used to detect presence or absence of a person or other being below the automated bedding system 10. For example, as arranged around the perimeter of the bed at both the first and second ends 14 and 16, a person or other body underneath the automated bedding system 10 may be detected by capacitive wire segment 24. In embodiments, based on detecting presence underneath the bedding system 10, bed articulation may be stopped. As viewed from the side in FIG. 3, the first and second segments 20 and 22 (hidden from view) create a defined sensing area on the top of the platform, near the first end 14, while the third segment 24 creates a defined sensing area on the bottom of the platform of the bedding system 10.

Figure 3:
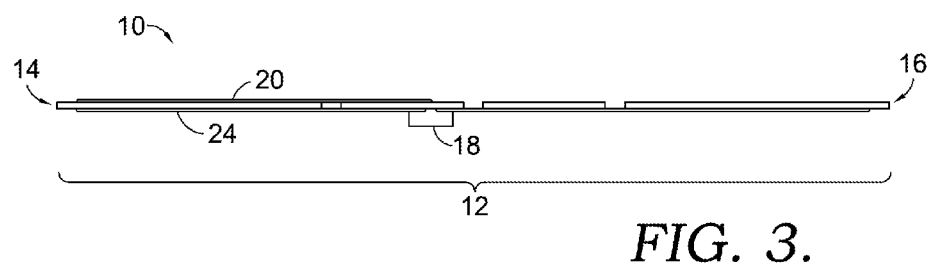
FIG. 3 is a side view of the automated bed platform of FIG. 1, with a capacitive wire coupled to the top and bottom of the platform, and the control enclosure coupled to the bottom of the platform.
Figure 4:
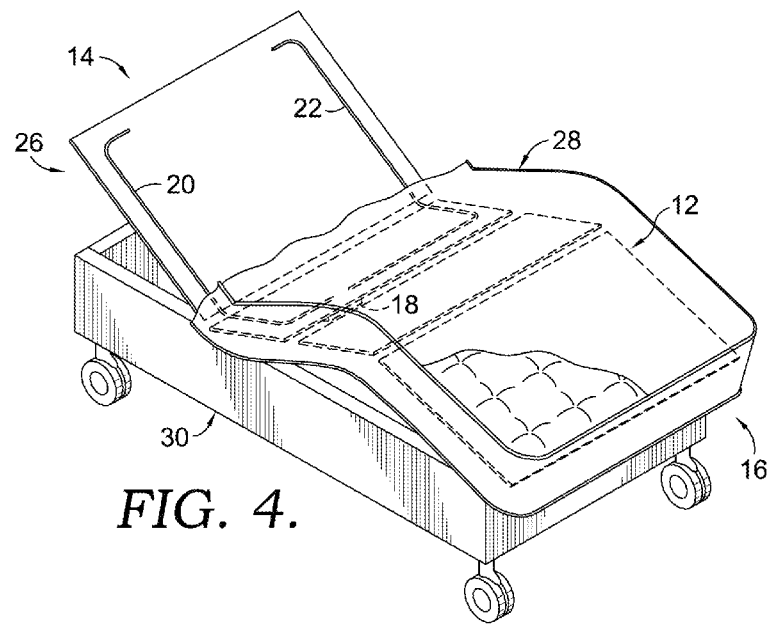
FIG. 4 is a perspective view of an automated bed with a portion of the mattress cut away to reveal the capacitive wire coupled to the top of the platform.

Referring next to FIG. 4, an adjustable bed 26 incorporates the automated bedding system 10 described with respect to FIGS. 1-3. The adjustable bed 26 includes a mattress 28 and a frame 30. A top portion of the mattress is cut away to reveal the first end 14 of the automated bedding system 10 platform, with the head of the bed partially raised. As described with reference to FIG. 1, capacitive wire segments 20 and 22 provide a defined sensing area near the first end 14, which detects a change in capacitance above the bed, such as the capacitance detected from a person resting on the bed.

Figure 5:
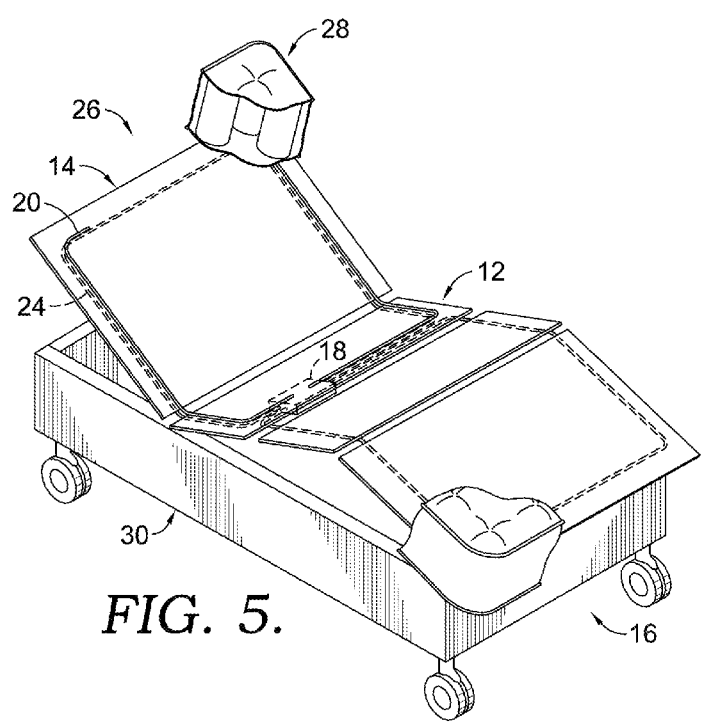
FIG. 5 is a perspective view of the automated bed of FIG. 4, with the mattress cut away to reveal the capacitive wire coupled to the top of the platform, and hidden lines indicating the capacitive wire and control enclosure coupled to the bottom of the platform.

FIG. 5 depicts the adjustable bed 26 from FIG. 4, with a majority of the mattress 28 removed. As can be seen on the plurality of panels 12, first and second segments 20 and 22 of capacitive wire detect presence above the platform (e.g. on top of the mattress), while the third segment 24 detects presence below the platform (e.g. under the bed). An enlarged view of FIG. 5 is shown in FIG. 6, with hidden lines depicting capacitive wires 20 and 24 coupled to the control enclosure 18, which is mounted beneath the panels 12.

In some embodiments, in alternative or in addition to positioning of capacitive wiring around the perimeter of the panels 12 that support an adjustable mattress, conductive wire is attached around the perimeter of the mattress itself. As shown in the adjustable bed 32 of FIG. 7, conductive wire may be incorporated into the tape edge surrounding the mattress 28. As such, the attached conductive wire may work as a sensor to detect presence of a person or other body near the perimeter of the mattress 28. For example, a conductive wire may be incorporated into the top tape edge 34 around the top surface of the mattress 28. In another example, a conductive wire may be incorporated into the bottom tape edge 36 around the bottom surface of the mattress 28. During manufacturing, a conductive wire may be inserted into the tape edge automatically, as the tape edge is applied to a mattress covering. In some embodiments, when routed through the tape edge perimeter, the sensitivity of the conductive wire may be adjusted in software associated with a processor used to determine presence detection.

The capacitive wire may be routed through some or all of the tape edge around the perimeter of a mattress 28. Additionally, a tape edge may be applied to both the top and bottom edges of the mattress 28, and both the top and bottom tape edges 34 and 36 may include a capacitive wire. Accordingly, the sensitivity of the capacitive wire in the top tape edge 34 may be adjusted independently from the tape edge 36 surrounding the perimeter of the bottom of the mattress. For example, a small change in voltage detected by the capacitive wires in the top tape edge 34 of the mattress may indicate that a user has moved on the surface of the mattress, but is still on the bed. By contrast, a small change in voltage detected by the capacitive wires in the bottom tape edge 36 of the mattress may indicate that a person, or other being, is below the bed. In either case, different features associated with the automated bedding system 10 may be activated based on whether presence is detected above the bed (via capacitive wires in the top tape edge 34) or below the bed (via capacitive wires in the bottom tape edge 36).

In further embodiments, a capacitive component may be incorporated into the mattress covering 38 of a mattress 28, as shown in FIG. 7. In particular, a capacitive thread may be sewn into the ticking on top of the mattress covering 38, as part of a sewn pattern. During manufacturing, a particular needle threaded with capacitive thread may be activated automatically and independently to incorporate the capacitive wire into a particular configuration on the surface of the mattress covering 38. For example, the capacitive thread may be sewn around a perimeter of the top surface of the mattress 28. In another example, the capacitive wire may be sewn in a pattern that creates perpendicular runs for capacitive detection. In one embodiment, capacitive thread sewn into the surface of a mattress covering 38 may terminate at a particular point and attach to a control enclosure 18. For example, an attachment may be used to crimp the mattress covering 38 material during sewing, to provide an attachment point for connecting the capacitive thread to a processor.

In some embodiments, a capacitive component may be incorporated into a platform-style bed. For example, a lower portion of a bed that does not articulate, such as a box spring or a mattress frame 30, may include a capacitive component that detects presence from above. In one embodiment, a capacitive wire is attached in a loop around the perimeter of the top of the frame 30, in FIG. 7. When a person or body is detected on top of the platform and/or frame 30, the articulating mattress 28 may discontinue lowering into contact with the frame 30. In one embodiment, a capacitive wire may be incorporated into the upholstery of a decorative surround (immovable frame). The sensitivity of the capacitive wire may be decreased so that direct contact is required with the edge of the surround before presence may be detected, in order to prevent false readings from a body approaching the frame.

Presence may also be detected using a loop of capacitive wire incorporated inside a mattress. For example, as shown in FIG. 8, a fourth segment 40 of capacitive wire may be incorporated inside an inner spring 42, and coupled to the control enclosure 18. While only one inner spring 42 is shown, it should be understood that capacitive wire could be incorporated into one or more of the many innersprings that make up a traditional mattress. As such, the loop of capacitive wire can detect a person or object in proximity to the loop, such as a person on the mattress, above the loop of capacitive wire.

A defined sensing area is created by routing of a capacitive wire around a perimeter of a furniture item, in a variety of configurations such as those described above. For example, a capacitive wire routed around the perimeter of a mattress, such as in the tape edge around a perimeter of the top surface of a mattress, creates a defined sensing area on the area of the mattress surrounded by the sensing perimeter. As such, a person's presence within the sensing area may be detected by the capacitive wire, which a processor may use to determine when a person exits or enters a bed. A processor coupled to the capacitive component may be housed in a control enclosure, such as control enclosure 18. In one embodiment, the control enclosure 18 is mounted below the platform of an automated bedding system 10. In further embodiments, the control enclosure 18 is mounted generally beneath the mattress 28.

In embodiments, capacitive wire incorporated into the perimeter of a mattress is used to monitor a change in capacitance over a specified amount of time. The capacitive component (capacitive wire) is adapted to have a voltage based on proximity of an object to the capacitive component. Such voltage information is collected via the capacitive component and received by the processor, which determines when a change in voltage satisfies a threshold. Once a particular change in capacitance satisfies a threshold, a corresponding function associated with the automated bed may be initiated. In embodiments, a threshold for initiating a corresponding function includes a particular amount of change in voltage within a particular amount of time. For example, when using capacitance information to turn lights on/off, a particular amount of change in voltage may be required during a particular amount of time before satisfying the threshold indicating that a person has exited the bed (and before the lights may be turned on). Similarly, a particular threshold value of voltage change may be required by the processor, over a particular amount of time, before making a determination that a person has re-entered the bed (and before the lights can be turned off again). In embodiments, a processor continuously receives capacitance monitoring information, and monitors how quickly a change in capacitance occurs (how quickly the delta changes) to determine if a big enough change has occurred in a certain amount of time to satisfy a threshold, and trigger the corresponding function.

Based on satisfying a particular threshold, various features associated with the automated bedding system 10 may be activated and/or enabled. For example, an alarm clock may only be triggered if a person's presence is detected in the bed (i.e. if a threshold amount of change in voltage is detected during capacitance monitoring over a particular amount of time). In another example, additional bedding features may be activated based on presence detection by capacitive wires. Such additional integrated bedding features include having a massage motor activated to wake up a user. If a user is not present in the bed, and therefore not detected using the capacitive wires, the lack of presence detection will prevent the massage motor from running at a particular scheduled time.

A variety of other functions of the automated bedding system 10 may be controlled based on detection with a capacitive wire. In other words, a processor coupled to the capacitive wire may initiate a variety of functions based on received data indicating presence or lack of presence, as determined using capacitance information. Different functions may be controlled, such as stopping a bed from articulating when presence is detected beneath the bed, turning on/off lights based on a person exiting/entering a bed, and controlling other accessories or electrical/household appliances through internal circuitry associated with the processor. In one example, after presence is no longer detected in the bed (thereby indicating that a person has exited the bed) lights may be turned on. Additionally, when the person returns to the bed, the lights may turn off.

A variety of communication protocols may be used to control the variety of functions described above. For example, a two-way controller using ZigBee® wireless communication protocol may be used. In some embodiments, a two-way communication protocol intended for use in automation (similar to Bluetooth®) may be utilized. One embodiment of the invention may be controlled by an external sensor only, with all of the components necessary for the sensor that plug into an existing motor. In another embodiment, two separate microcontrollers may be used: one dedicated primarily for sensing purposes that, when it detects something, sends a signal to a secondary device/microcontroller that is programmed to initiate the corresponding response.

Figure 9:
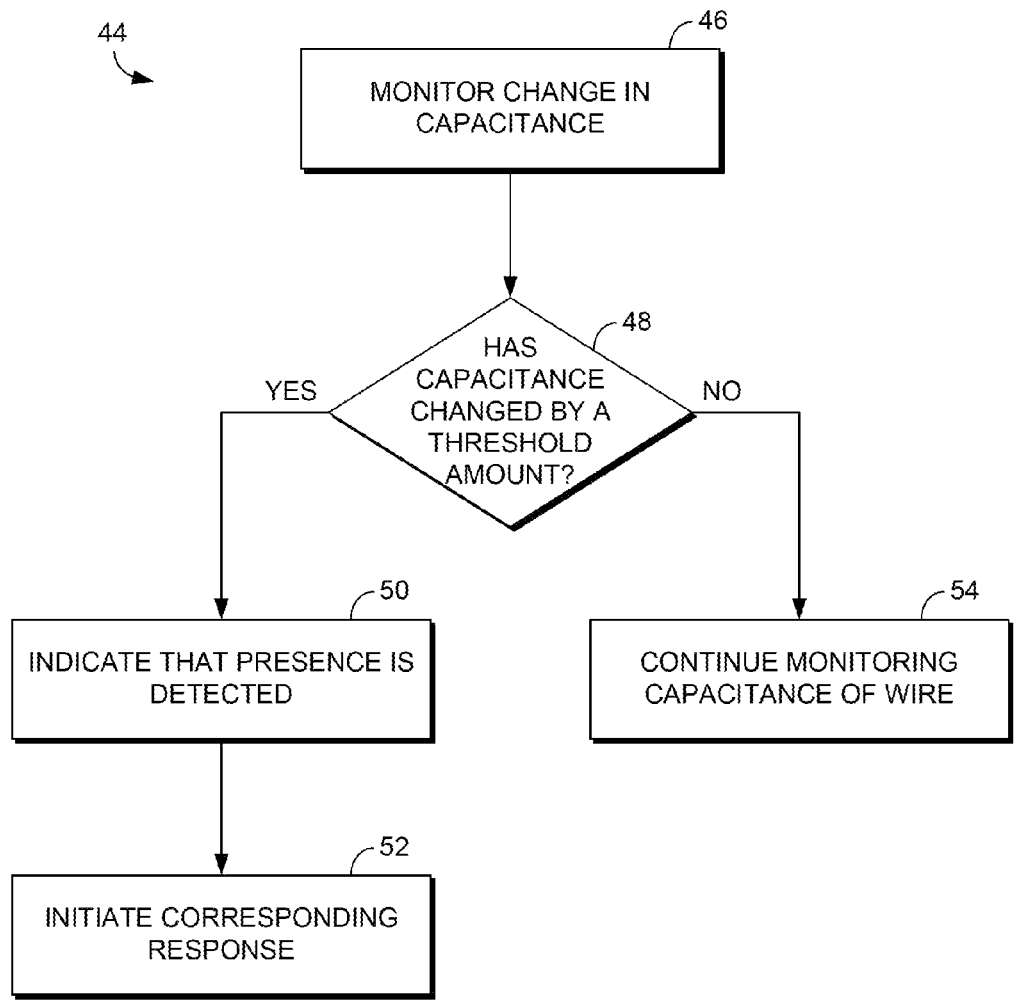
FIG. 9 is a flow diagram of an exemplary method of detecting presence with respect to a bed.

Turning now to FIG. 9, an exemplary flow diagram 44 depicts monitoring capacitance and making a determination of presence with respect to a furniture item. At block 46, an average change in capacitance is monitored using a capacitive wire. As discussed above, the change in capacitance indicates a change in voltage over a particular amount of time. At block 48, a determination is made regarding whether the capacitance has changed by a threshold amount. If a determination is made that the capacitance has changed by a threshold amount (i.e. a particular amount of change in voltage has occurred within a particular window of time), then an indication is made that presence has been detected at block 50, and the corresponding response is initiated at block 52. As will be understood, blocks 50 and 52 may, in some embodiments, be combined into a single step of initiation of the corresponding response based on a determination of presence detection. At block 54, if capacitance has not changed by a threshold amount, capacitance monitoring continues.

Figure 10:
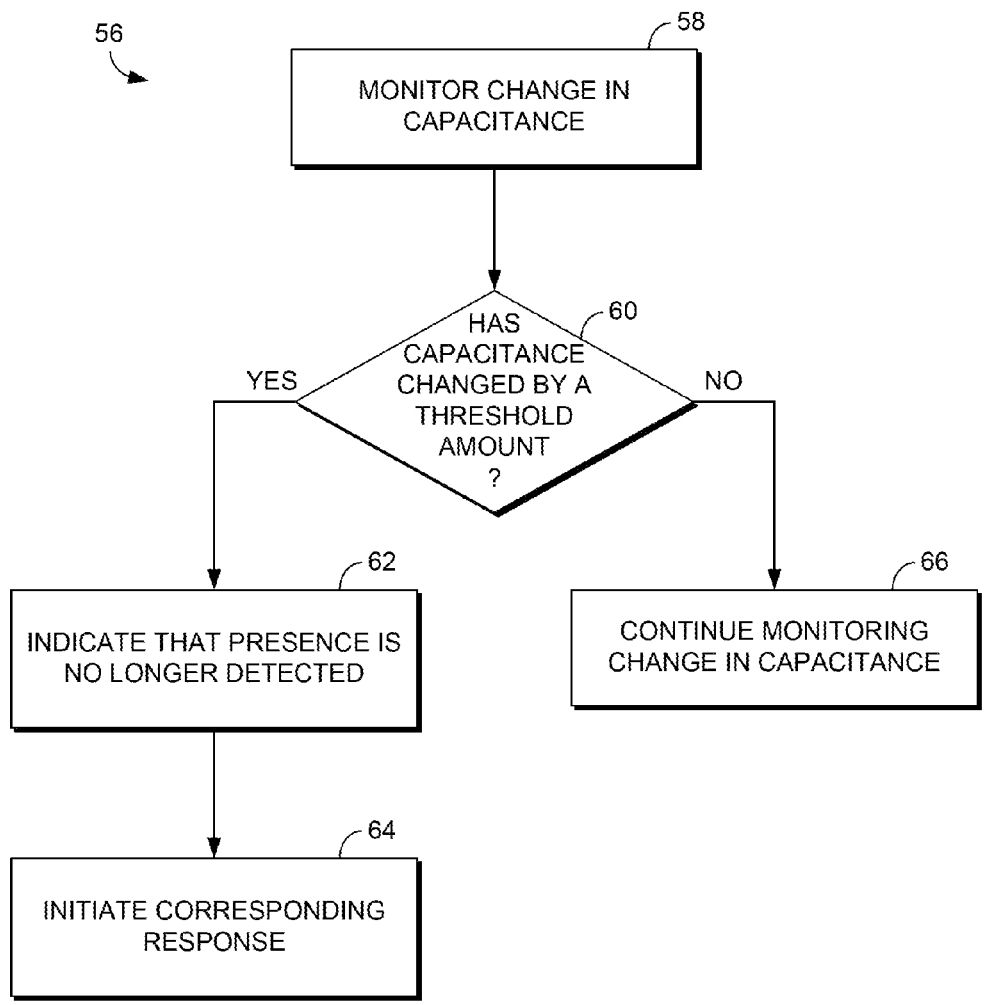
FIG. 10 is a flow diagram of an exemplary method of detecting presence with respect to a bed.

With reference finally to FIG. 10, an exemplary flow diagram 56 depicts monitoring capacitance and making a determination that presence is no longer detected with respect to a furniture item. At block 58, an average change in capacitance is monitored using a capacitive wire. At block 60, a determination is made whether capacitance has changed by a threshold amount. At block 62, if capacitance has changed by a threshold amount, an indication that presence is no longer detected is made at block 62, and a corresponding response is initiated at block 64. At block 66, if it is determined that the threshold amount has not been satisfied, capacitance monitoring continues.

As will be understood, a variety of filtering techniques may be utilized to adjust the determinations made (regarding whether presence is or is not detected) using software associated with the processor. For example, a variety of filters or transforms may be applied to the monitored capacitance signal in order to adjust/adapt the software for a particular application or user. For example, an automated bedding system could be adapted to adjust lighting or other functions based on particular amounts of change in capacitance over particular amounts of time, or trigger particular functions during particular times of day/night. As such, a processor may be trained to alter the sensitivity of a threshold based on previous use by a particular user of a corresponding feature. Additionally, a reaction time may be changed and a threshold may be adjusted for different users and different features of the automated bed.

From the foregoing, it will be seen that this invention is one well adapted to attain all the ends and objects hereinabove set forth together with other advantages, which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

The invention claimed is:
1. An adjustable bed, comprising:
a mattress support that comprises a plurality of support panels, at least one of said support panels movable relative to the other ones of said support panels to thereby adjust the bed, wherein the adjustable bed comprises a head end, a foot end opposite and parallel to the head end, a first side perpendicular to the head end and the foot end, and a second side perpendicular to the head end and the foot end;
a mattress resting on top of the mattress support, said mattress separate from the mattress support that the mattress is resting on top of, said mattress having a covering material disposed over at least a top surface of the mattress;
at least one capacitive component coupled to the bed, said coupling to the bed comprising the at least one capacitive component on a perimeter of at least one of the plurality of support panels to provide a defined sensing area based on a position of the at least one capacitive component around the perimeter, said perimeter of at least one of the plurality of support panels comprising at least a portion of an outer edge of the first side, at least a portion of an outer edge of the second side, and at least a portion of an outer edge of one or more of the head end and the foot end, wherein the at least one capacitive component is adapted to have a voltage based on proximity of an object to the at least one capacitive compo- nent, and further wherein the at least one capacitive component is configured to detect user occupancy with respect to the mattress; and a processor coupled to the at least one capacitive component, the processor adapted to receive information provided by the at least one capacitive component and to determine that a change in voltage satisfies a threshold.

2. The bed of claim 1, wherein the at least one capacitive component is directly coupled to at least a portion of a perimeter of a top of at least one of the plurality of support panels.

3. The bed of claim 1, wherein the at least one capacitive component is directly coupled to at least a portion of a perimeter of a bottom of at least one of the plurality of support panels.

4. The bed of claim 1, wherein the at least one capacitive component is coupled to at least a portion of a tape edge surrounding a perimeter of the top surface of the mattress, the tape edge coupled to the covering material.

5. The bed of claim 1, wherein the at least one capacitive component is interwoven with the covering material.

6. The bed of claim 1, wherein the at least one capacitive component comprises a wire.

7. The bed of claim 1, wherein the at least one capacitive component is coupled to at least one spring inside the mattress.

8. The bed of claim 1, wherein the processor comprises a control enclosure coupled to a bottom of at least one of the plurality of support panels.

9. The bed of claim 1, wherein the processor receives information directly from the at least one capacitive component.

10. The bed of claim 1, wherein determining that a change in voltage satisfies a threshold comprises:
monitoring a change in voltage detected by the at least one capacitive component over a particular period of time; and
comparing the change in voltage over the period of time with the threshold.

11. A method for detecting presence with respect to an adjustable bed, the method comprising:
receiving information provided by at least one capacitive component coupled to an outer perimeter of the adjustable bed, wherein the at least one capacitive component is adapted to have a voltage based on proximity of an object to the at least one capacitive component, wherein the adjustable bed comprises a mattress support that comprises a plurality of support panels, at least one of said support panels movable relative to the other ones of said support panels to thereby adjust the adjustable bed, and a mattress resting on a top surface of the mattress support, said mattress comprising a covering material disposed over at least a top surface of the mattress, wherein the at least one capacitive component comprises one or more of:
(1) at least one capacitive component on a perimeter of at least a portion of a top of at least one of the plurality of support panels to provide a first defined sensing area based on a position of the at least one capacitive component around the perimeter with respect to the top of the plurality of support panels, said at least one capacitive component of the first defined sensing area configured to detect user occupancy with respect to the mattress;
(2) at least one capacitive component on a perimeter of a top tape edge surrounding a perimeter of the top surface of the mattress to provide a second defined sensing area based on a position of the at least one capacitive component around the perimeter with respect to the top of the mattress, said top tape edge directly coupled to the covering material, said at least one capacitive component of the second defined sensing area configured to detect user occupancy with respect to the mattress; and
(3) at least one capacitive component on a perimeter of a bottom tape edge surrounding a perimeter of a bottom surface of the mattress to provide a third defined sensing area based on a position of the at least one capacitive component around the perimeter with respect to the bottom of the mattress, said bottom tape edge directly coupled to the covering material, said at least one capacitive component of the third defined sensing area configured to detect user occupancy with respect to the mattress;
determining that a change in voltage satisfies a threshold amount; and
based on determining that the threshold amount is satisfied, initiating a corresponding response,
wherein the at least one capacitive component is configured to detect user occupancy with respect to the mattress.

12. The method of claim 11, wherein determining that a change in voltage satisfies a threshold amount comprises comparing an average voltage detected over a particular amount of time with the threshold amount.

13. The method of claim 12, wherein the threshold amount indicates that either
1) presence is detected in proximity to the bed, or
2) presence is no longer detected in proximity to the bed.

14. The method of claim 13, wherein initiating a corresponding response comprises:
activating at least one function associated with the bed based on a determination that presence is detected in proximity to the bed, or
activating at least one function associated with the bed based on a determination that presence is no longer detected in proximity to the bed.

15. A bed comprising:
a mattress having a covering material disposed over at least a top surface of the mattress;
a top tape edge surrounding an outer perimeter of the top surface of the mattress, the top tape edge coupled to the covering material;
at least one mattress top capacitive component coupled to at least a portion of the top tape edge to provide a defined sensing area based on a position of the mattress top capacitive component around an outer perimeter of the bed, wherein the at least one mattress top capacitive component is adapted to have a voltage based on proximity of an object to the at least one mattress top capacitive component, wherein the at least one mattress top capacitive component is configured to detect user occupancy with respect to the mattress;
a processor coupled to the at least one mattress top capacitive component, the processor adapted to receive information provided by the at least one mattress top capacitive component and to determine that a change in voltage satisfies a threshold;
a mattress support comprising a plurality of support panels, at least one of said support panels movable relative to the other ones of said support panels to thereby adjust the bed, wherein the mattress rests on top of the mattress support, wherein the bed comprises a head end, a foot end opposite and parallel to the head end, a first side perpendicular to the head end and the foot end, and a second side perpendicular to the head end and the foot end; and
at least one mattress support capacitive component on a perimeter of at least one of the plurality of support panels to provide a defined sensing area based on a position of the at least one mattress support capacitive component around the perimeter, said perimeter of at least one of the plurality of support panels comprising at least a portion of an outer edge of the first side, at least a portion of an outer edge of the second side, and at least a portion of an outer edge of one or more of the head end and the foot end, wherein the at least one mattress support capacitive component is adapted to have a voltage based on proximity of an object to the at least one mattress support capacitive component, and further wherein the at least one mattress support capacitive component is configured to detect user occupancy with respect to the mattress.

16. The bed of claim 15, further comprising:
a bottom tape edge surrounding an outer perimeter of a bottom surface of the mattress, the bottom tape edge coupled to the covering material; and
at least one mattress bottom capacitive component coupled to at least a portion of the bottom tape edge to provide a defined sensing area based on a position of the mattress bottom capacitive component around the outer perimeter of the bed, wherein the at least one mattress bottom capacitive component is adapted to have a voltage based on proximity of an object to the at least one mattress bottom capacitive component,
wherein the processor is coupled to the at least one mattress bottom capacitive component and is adapted to receive information provided by the at least one mattress bottom capacitive component and to determine that a change in voltage satisfies a threshold.

\* \* \* \* \*